(12) United States Patent
Lee et al.

(10) Patent No.: US 7,456,282 B2
(45) Date of Patent: Nov. 25, 2008

(54) 2-AMINO-9-(2-SUBSTITUTED ETHYL)PURINES AND PREPARING METHODS FOR 9-[4-ACETOXY-3-(ACETOXYMETHYL)BUT-1-YL]-2-AMINOPURINE USING THE SAME

(75) Inventors: Byoung-Suk Lee, Seoul (KR); Sang-Hoon Shin, Gwacheon (KR); Jong-Sik Park, Seoul (KR)

(73) Assignee: Kyungdong Pharm. Co., Ltd. (KR)

( * ) Notice: Subject to any disclaimer, the term of this patent is extended or adjusted under 35 U.S.C. 154(b) by 458 days.

(21) Appl. No.: 10/554,676

(22) PCT Filed: Jun. 12, 2004

(86) PCT No.: PCT/KR2004/001405

§ 371 (c)(1), (2), (4) Date: Oct. 26, 2005

(87) PCT Pub. No.: WO2004/110343

PCT Pub. Date: Dec. 23, 2004

(65) Prior Publication Data

US 2006/0258862 A1 Nov. 16, 2006

(30) Foreign Application Priority Data

Jun. 13, 2003 (KR) ............ 10-2003-0038417

(51) Int. Cl.
*C07D 473/32* (2006.01)

(52) U.S. Cl. .................................... 544/277
(58) Field of Classification Search ........... 544/277
See application file for complete search history.

(56) References Cited

OTHER PUBLICATIONS

Clayette et al, Antiviral Chemistry & Chemotherapy (1991), 2(6), 329-36.*
Dille et al., Journal of Organic Chemistry (1955), 20, 171-7.*
Lister et al, Journal of the Chemical Society (1960) 327-31.*

\* cited by examiner

*Primary Examiner*—Mark L Berch
(74) *Attorney, Agent, or Firm*—Galgano & Associates, PLLC

(57) ABSTRACT

The present invention relates to a new compound of 2-amino-9-(2-substituted ethyl)purine and an effective method for preparing 9-[4-acetoxy-3-(acetoxymethyl)but-1-yl]-2-aminopurin (famciclovir) using the same. The 2-amino-9-(2-substituted ethyl)purine according to the invention is represented by the following formula (II'): (Formula II') wherein R is a hydroxy, halogen, mesyloxy or tosyloxy group. The inventive method for the preparation of famciclovir comprises the steps of halogenating 2-amino-9-(2-substituted ethyl)purine to give 2-amino-9-(2-halogenoethyl)purine, and reacting the halogenated compound with diethylmalonate. The inventive preparation method allows famciclovir, a purine derivative drug with effective antiviral activity, to be prepared in a high selectivity of 100% in a pure form by using the inventive new compound of 2-amino-9-(2-substituted ethyl)purine. In addition, the inventive method allows the utilization of relatively mild reaction conditions, and thus, has high industrial process efficiency.

23 Claims, No Drawings

2-AMINO-9-(2-SUBSTITUTED ETHYL)PURINES AND PREPARING METHODS FOR 9-[4-ACETOXY-3-(ACETOXYMETHYL)BUT-1-YL]-2-AMINOPURINE USING THE SAME

TECHNICAL FIELD

The present invention relates to a new compound of 2-amino-9-(2-substituted ethyl)purine and an effective method for preparing 9-[4-acetoxy-3-(acetoxymethyl)but-1-yl]-2-aminopurine using the same. More particularly, the present invention relates to an effective method for preparing famciclovir of the following formula (I) using 2-amino-9-(2-substituted ethyl)purine of the following formula (II'), by which famciclovir can be prepared in high selectivity and high process efficiency under relatively mild reaction conditions:

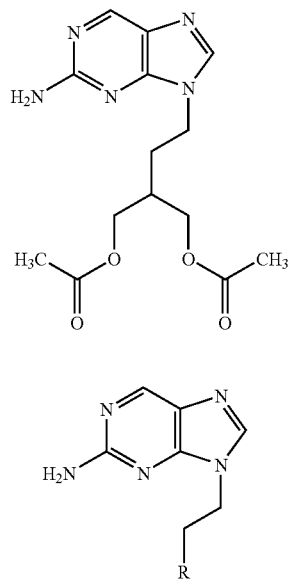

[Formula I]

[Formula II']

wherein R represents hydroxy, halogen, mesyloxy or tosyloxy.

BACKGROUND ART

Typical examples of the prior art on the preparation of the compound of formula (I), i.e., famciclovir, include European Patent No. 182,024, and U.S. Pat. Nos. 5,684,153, 5,138,057 and 5,917,041.

European Patent No. 182,024 and U.S. Pat. No. 5,684,153 disclose a method for preparing 9-[4-acetoxy-3-(aectoxymethyl)but-1-yl]-2-aminopurine as shown in the following reaction scheme (1), in which 2-amino-6-chloropurine of the following formula (VIII) is reacted with 2-acetoxymethyl-4-halobut-1-yl-acetate of the following formula (IX) to give 9-[4-acetoxy-3-(acetoxymethyl)but-1-yl]-2-amino-6-chloropurine of the following formula (X), which is then reduced into the compound of formula (I) in the presence of palladium as a reduction catalyst:

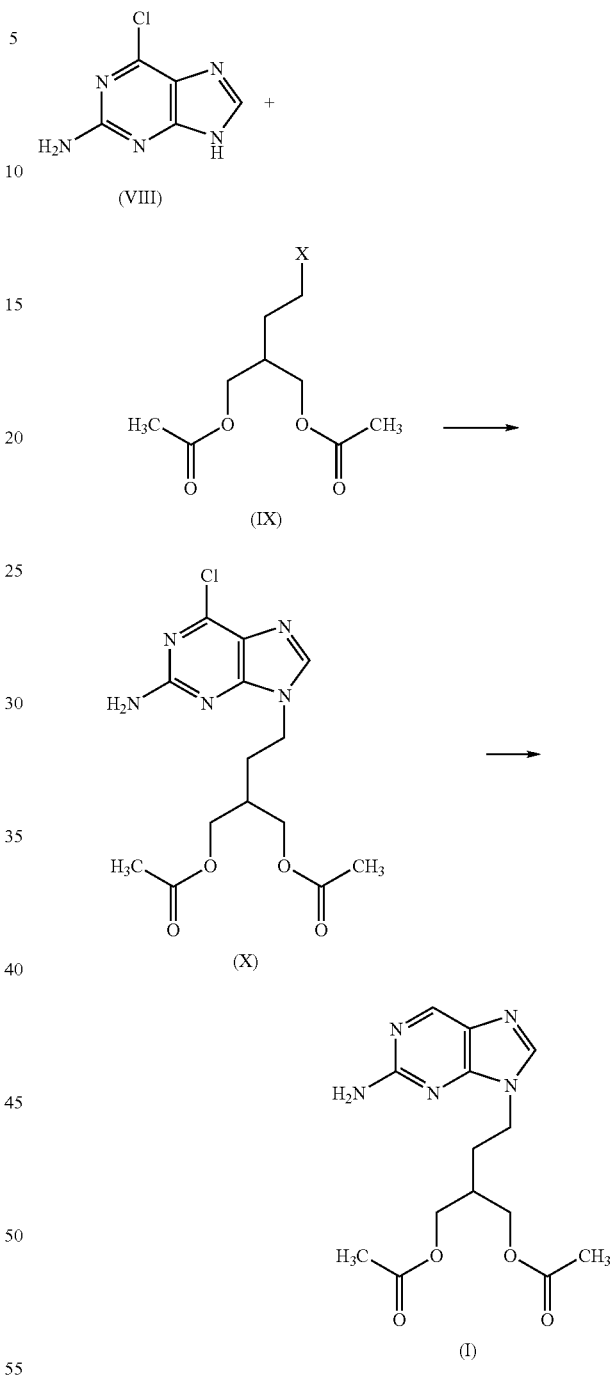

[Reaction Scheme 1]

wherein X is a halogen atom.

However, the above preparation method has a severe problem in that, as shown in the following reaction scheme (2), the reaction between the compound of formula (VI II) and the compound of formula (IX) produces not only the compound of formula (X) but also its isomer, 7-[4-acetoxy-3-(acetoxymethyl)but-1-yl]-2-amino-6-chloropurine of the following formula (XI), at a ratio of 80%:20%, indicating that selectivity for the compound (X) is low and the purification of the compound (X) becomes very difficult:

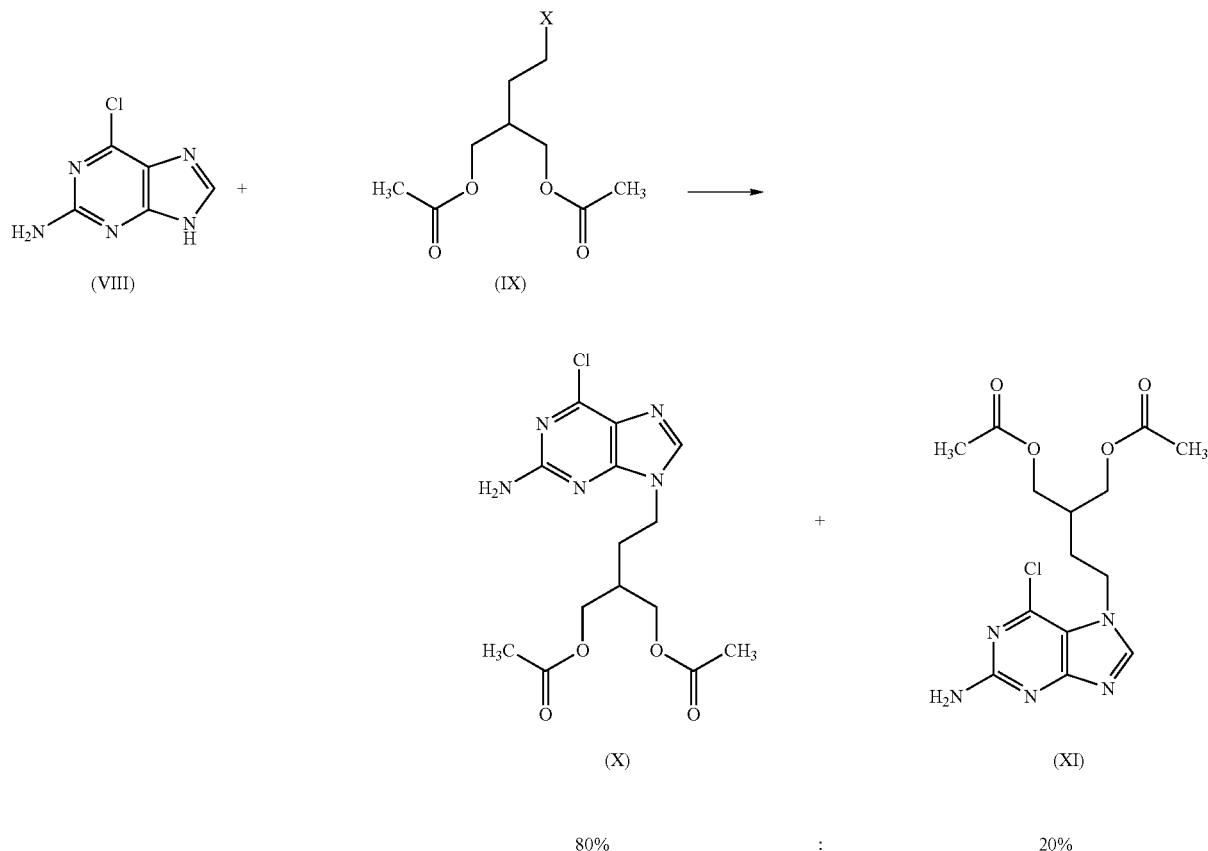

wherein X is a halogen atom.

Furthermore, the preparation method shown in reaction scheme (1) has a severe problem in that a palladium catalyst, which is highly explosive, must be used in the preparation of the final desired compound of formula (1) from the compound of formula (X). Thus, this method has low process efficiency which makes its industrial application unsuitable.

Meanwhile, U.S. Pat. No. 5,138,057 discloses a method for preparing 9-[4-acetoxy-3-(aectoxymethyl)but-1-yl]-2-aminopurine of the following formula (I) as shown in the following reaction scheme (3), in which 2-amino-6,8-dichloropurine of the following formula (XII) is reacted with 2-acetoxymethyl-4-halobut-1-yl-acetate of the following formula (IX) to yield 9-[4-acetoxy-3-(acetoxymethyl)but-1-yl]-2-amino-6,8-dichloropurine of the following formula (XIII) which is then reduced using palladium as a reduction catalyst under a high-pressure condition:

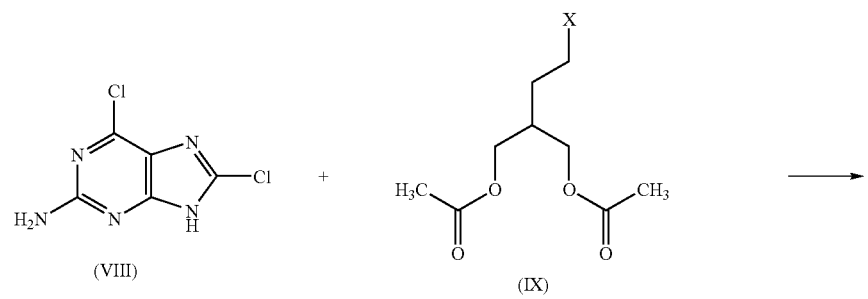

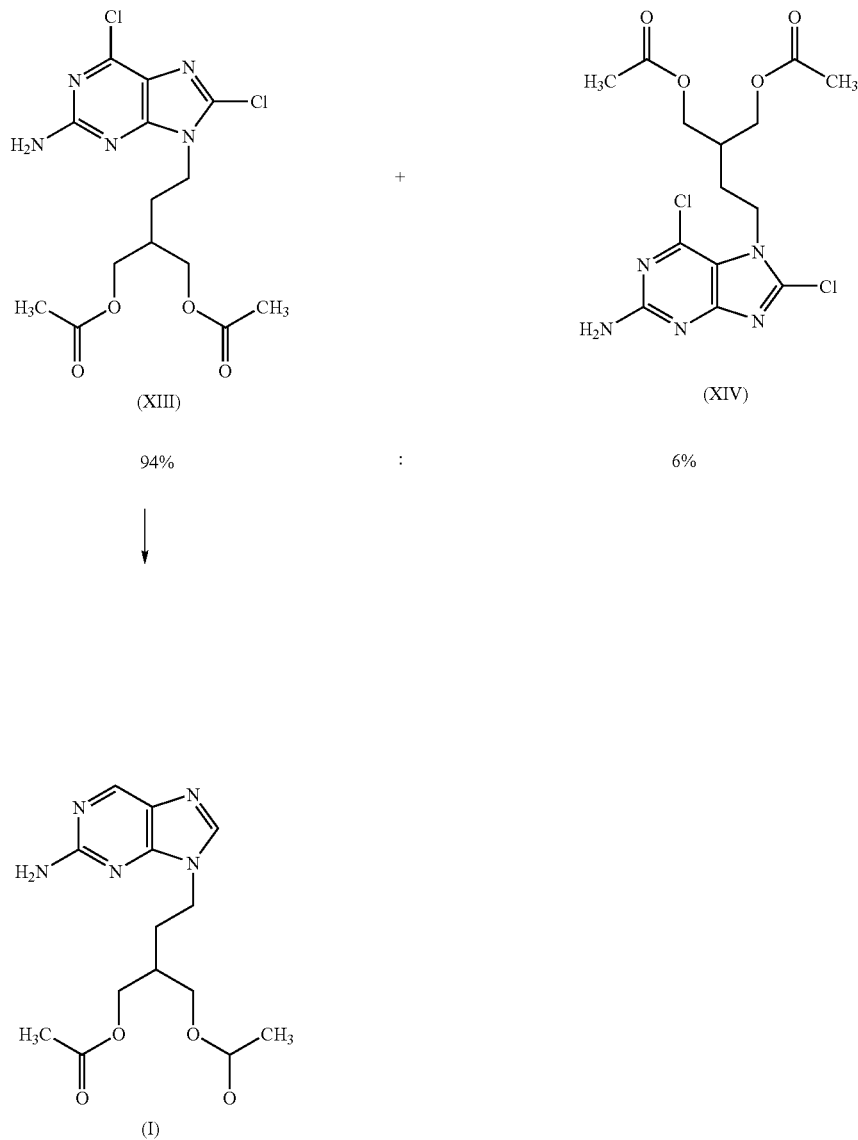

(XIII) 94%  :  (XIV) 6%

↓

(I)

wherein X is a halogen atom.

In this method, by the reaction between the compound of formula (XII) and the compound of formula (IX), not only the compound of formula (XIII) but also its isomer, 7-[4-acetoxy-3-(acetoxymethyl)but-1-yl]-2-amino-6,8-dichloropurine are produced at a ratio of 94%:6% indicating a somewhat increase in selectivity. However, this method, as in European Patent No. 182,024 and U.S. Pat. No. 5,684,153, also has a severe problem in that the preparation of the final desired compound of formula (I) from the compound of formula (XIII) must be carried out in the presence of a highly explosive palladium catalyst under a high-pressure condition (above 50 psi). For this reason, the industrial application of this method is still difficult.

Furthermore, U.S. Pat. No. 5,971,041 discloses a method for preparing 9-[4-acetoxy-3-(aectoxymethyl)but-1-yl]-2-aminopurine of the following formula (1) as shown in the following reaction scheme (4), in which (N-(2-amino-4,6-dichloro-5-pyrimidinyl)formamide of the following formula (XV) is reacted with 2-Acetoxymethyl-4-aminobut-1-yl-acetate of the following formula (XVI) to give a compound of the following formula (XVII), which is then converted into 9-[4-acetoxy-3-(acetoxymethyl)but-1-yl]-2-amino-6-chloropurine using triethylorthoformate of the following formula (XVIII), which is, in turn, reduced into the compound of formula (I) using palladium as a reduction catalyst:

[Reaction Scheme 4]

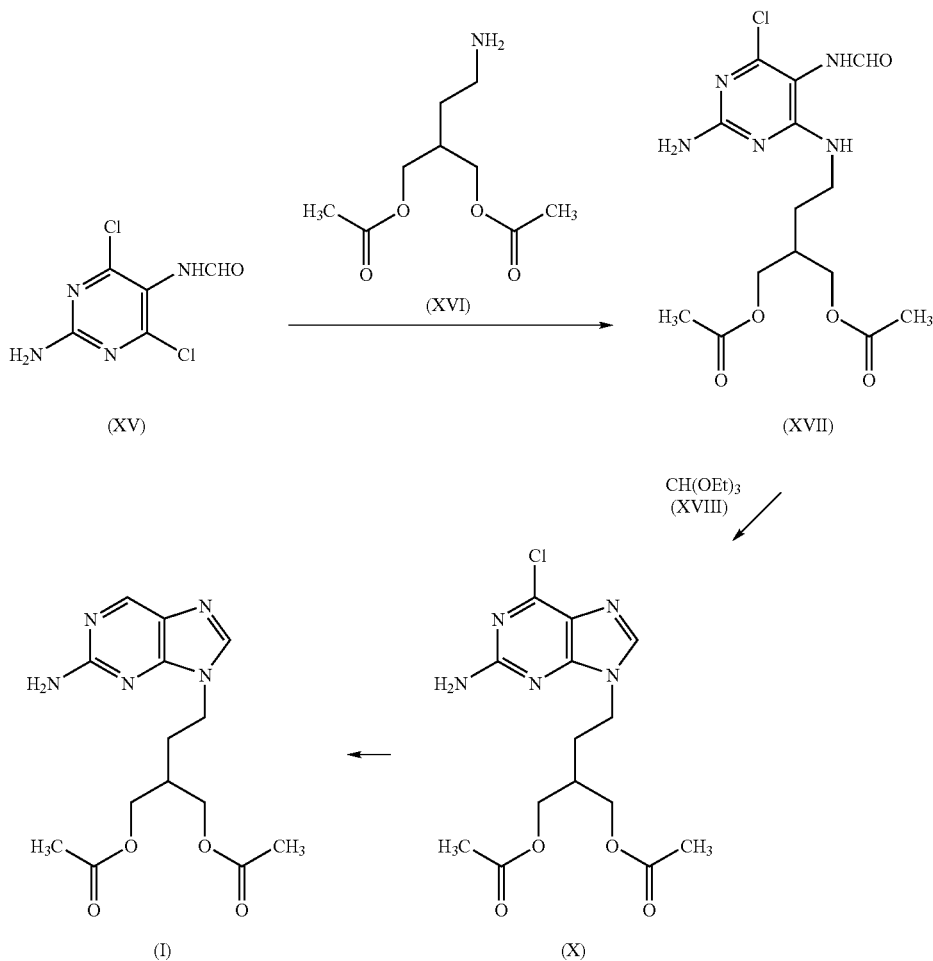

However, this method has problems in that, as shown in the following reaction GIBSON scheme (5), 2,5-diamino-4,6-dihydroxypyrimidine of the following formula (XIX) and chloromethylene iminium salt of the following formula (XX), which are expensive, must be used to prepare the compound of formula (XV) as a starting material, and the final desired compound of formula (I) is obtained at a very low yield of about 32% through several steps from the compound of formula (XXI). Another problem is that the palladium catalyst, which is highly explosive, must be used, as in the prior methods disclosed in EP No. 182,024 and U.S. Pat. No. 5,684,153. Thus, this method has low process efficiency and a long reaction pathway, which make its industrial application difficult.

[Reaction Scheme 5]

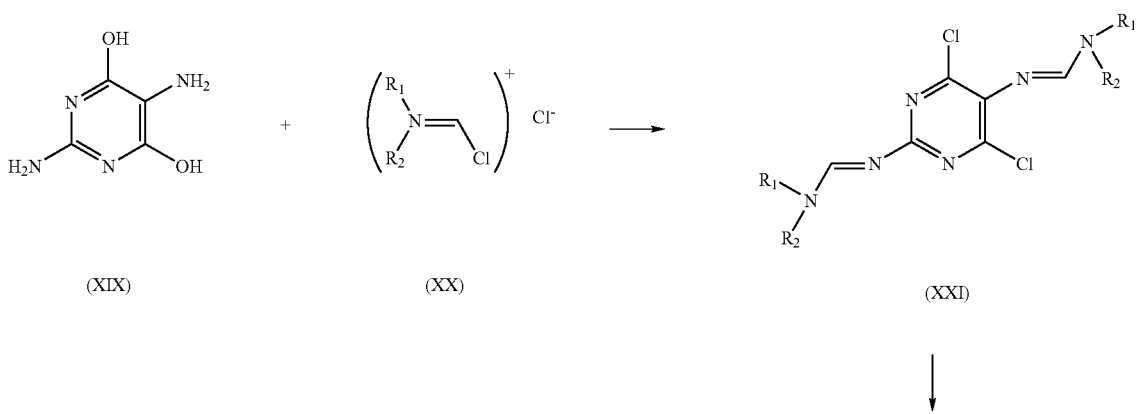

-continued

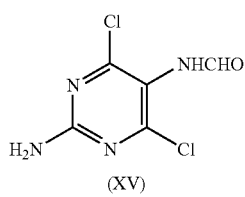 (XV)

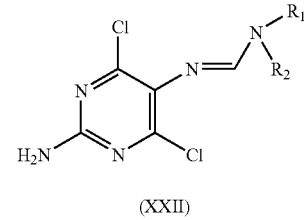 (XXII)

DISCLOSURE OF INVENTION

Therefore, a first object of the present invention is to provide a new compound which can be effectively used in the preparation of famciclovir, an antiviral purine derivative drug.

A second object of the present invention is to provide a method for the preparation of famciclovir, which has high selectivity leading to high process efficiency.

A third object of the present invention is to provide a method for the preparation of famciclovir, which allows the utilization of relatively mild reaction conditions and thus has high process efficiency.

Hereinafter, the present invention will be described in detail.

The present invention relates to a new compound of 2-amino-9-(2-substituted ethyl)purine of the following formula (II'), and a method for effectively preparing 9-[4-acetoxy-3-(acetoxymethyl)but-1-yl]-2-aminopurine (called 'famciclovir') of the following formula (I) using the same, in which the famciclovir is a purine derivative drug with effective antiviral activity (see European Patent No. 141,927):

[Formula I]

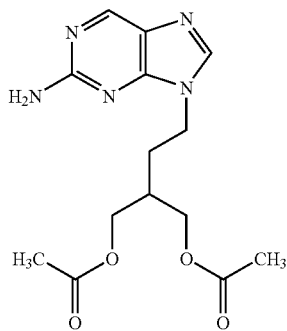

[Formula II']

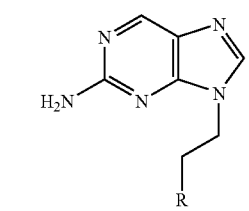

wherein R is a hydroxy, halogen, mesyloxy or tosyloxy group.

In the inventive method for preparing famciclovir using the new compound of 2-amino-9-(2-substituted ethyl)purine of formula (II'), the compound of formula (II') shows 100% selectivity, so that 7-[4-acetoxy-3-(acetoxymethyl)but-1-yl]-2-aminopurine of the following formula (XXIII), which is an isomer of the famciclovir represented by formula (I) and has no pharmacological activity, is not produced as a byproduct in a preparation process of famciclovir. Thus, the desired compound, famciclovir, can be prepared in a high selectivity of 100%.

[Formula XXIII]

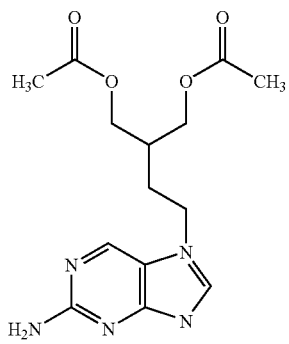

If the inventive compound of formula (II') is, for example, 2-amino-9-(2-hydroxyethyl)purine of the following formula (II) or 2-amino-9-(2-halogenoethyl)purine of the following formula (III), the famciclovir of formula (I) as the desired compound can be prepared in 100% selectivity by a preparation method which is generally described just below. Namely, this preparation method comprises: halogenating 2-amino-9-(2-hydroxyethyl)purine of the following formula (II) to give 2-amino-9-(2-halogenoethyl)purine of the following formula (III), subjecting the compound of formula (III) to substitution reaction with diethylmalonate of the following formula (IV) to give 2-amino-9-(ethyl 2-carboethoxybutanoate-4-yl)purine of the following formula (V), reducing the compound of formula (V) to give 2-amino-9-[4-hydroxy-3-(hydroxymethyl)but-1-yl]purine of the following formula (VI), and acetylating the compound of formula (VI):

[Formula II]

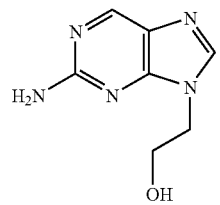

[Formula III]

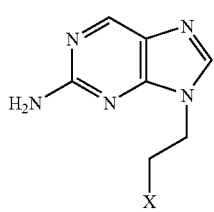

(X is a halogen atom)

[Formula IV]

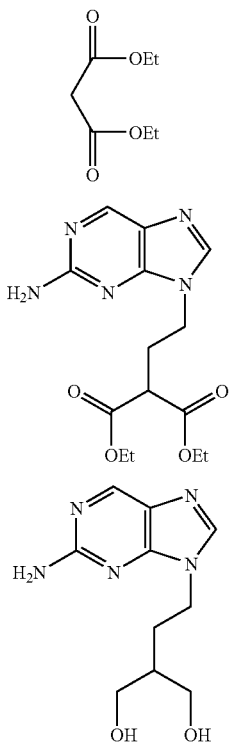

The compounds of formulas II and III in the above general description about the inventive preparation method are core materials in the inventive preparation methods. The compound of formula (II) contains no a mino-7-(2-hydroxyethyl)purine) of the following formula (VII), which is its isomer, and thus, it has a high selectivity of 100%.

[Formula VII]

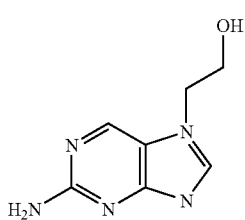

The compounds of formula (II') may also be compounds having various substituents, such as 2-amino-9-(2-mesyloxyethyl)purine of the following formula (XXVI) or 2-amino-9-(2-tosyloxyethyl)purine of the following formula (XXVII), in addition to 2-amino-9-(2-hydroxyethyl)purine of formula (II). Any of such compounds is highly useful as an intermediate for the preparation of a purine derivative drug, such as famciclovir with antiviral and antibacterial activities.

[Formula XXVI]

[Formula XXVII]

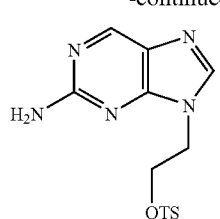

Any of the compounds of formula (II), (XXVI) and (XXVII), which are preferred examples of the compound of formula (II'), is converted into 2-amino-9-(2-halogenoethyl)purine by halogenation.

Meanwhile, the halogen in 2-amino-9-(2-halogenoethyl) purine of formula (III) is not specifically limited, but is most preferably bromine in view of the following advantages: (1) the preparation of the compound (III) is easy, (2) a reaction process is very efficient, and (3) a brominating agent results in a very high yield of more than 90%. Of the derivatives of formula (III), 2-amino-9-(2-bromoethyl)purine having a bromine substituent is represented by the following formula (III-1):

[Formula III-1]

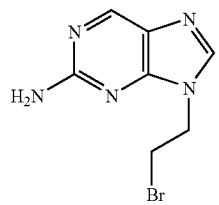

Hereinafter, the preparation Method according to the present invention will be described in more detail with reference to the following reaction scheme 6, by way of an example where the new inventive compound of formula (II') is 2-amino-9-(2-hydroxyethyl)purine of formula (II) or 2-amino-9-(2-halogenoethyl)purine of formula (III).

As shown in reaction scheme 6 below, 2-amino-9-(2-hydroxyethyl)purine of formula (II) is reacted with a halogenating agent, such as carbon tetrachloride, sodium iodide, potassium iodide, triphenylphosphine dibromide, carbon tetrabromide, or N-bromosuccinimide, in a polar or nonpolar organic solvent, at a temperature of about 0-100° C., and preferably about 20-40° C., for about 2-10 hours, and preferably about 3-5 hours, to give 2-amino-9-(2-halogenoethyl) purine of formula (III). The compound of formula (III) is then reacted with diethylmalonate of formula (IV) in the presence of a base, such as potassium carbonate, sodium carbonate, sodium methoxide or sodium ethoxide, in a polar organic solvent, at a temperature of about 0-100° C., and preferably 40-60° C., for about 2-10 hours, and preferably about 3-5 hours, to give 2-amino-9-(ethyl 2-carboethoxybutanoate-4-yl)purine of formula (V). Then, the compound of formula (V), after separation or without separation, is reacted with a reducing agent, such as sodium borohydride or lithium aluminum hydride, in a polar or nonpolar organic solvent, at a temperature of about 0-100° C., and preferably about 40-60° C., for about 2-10 hours, and preferably about 3-5 hours, to give 2-amino-9-[4-hydroxy-3-(hydroxymethyl)but-1-yl]purines of formula (VI). Then, the compound of formula (VI) is reacted with acetic acid anhydride in a nonpolar organic solvent at a temperature of about 0-100° C., and preferably about 20-40° C., for about 2-10 hours, and preferably about 3-5 hours, to produce the final desired compound (famciclovir) of formula (I).

[Reaction Scheme 6]

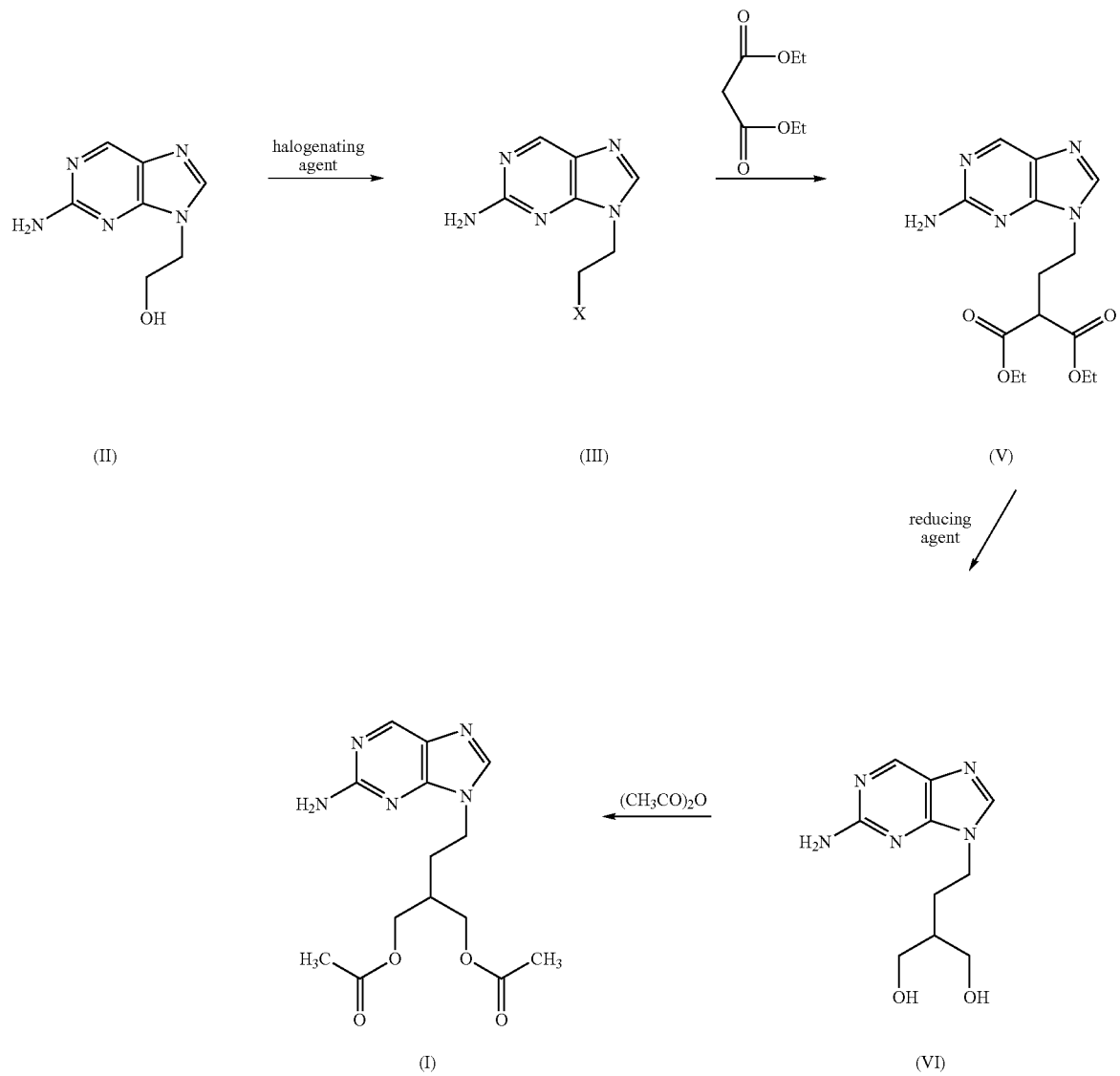

wherein X is a halogen atom.

Preferred examples of the polar organic solvent which is used in the inventive preparation method include N,N-dimethylformamide, dimethylsulfoxide, acetonitrile, pyridine, acetic acid, and lower alcohol solvents with 1 to 3 carbon atoms, such as methanol, ethanol or isopropanol, and a mixture thereof. Preferred examples of the nonpolar organic solvent include ethylether, tetrahydrofuran, toluene, benzene, 1,4-dioxane, chloroform, dichloromethane, and a mixture thereof.

Meanwhile, the compound of formula (II') which is used as a starting material in the inventive preparation method is a new material, and its preparation method will now be described in brief with reference to the following reaction scheme (7) by way of an example where the compound of formula (II') is 2-amino-9-(2-hydroxyethyl)purine.

As shown in reaction scheme (7) below, 2-amino-4-(2-hydroxyethylamino)-5-nitropyrimidine is reacted with a reducing agent, such as Raney-nickel or iron powder, in a polar organic solvent at a temperature of about 0-100° C., and preferably about 30-50° C., for about 1-10 hours, and preferably about 2-5 hours, to give 2,5-diamino-4-(2-hydroxyethylamino)pyrimidine of formula (XXV). Then, the compound of formula (XXV) is allowed to react immediately without separation, in triethylorthoformate of formula (XVIII) at a temperature of about 50-150° C., and preferably about 70-90° C., for about 5-15 hours, and preferably about 8-10 hours, to give 2-amino-9-(2-hydroxyethyl)purine.

[Reaction Scheme 7]

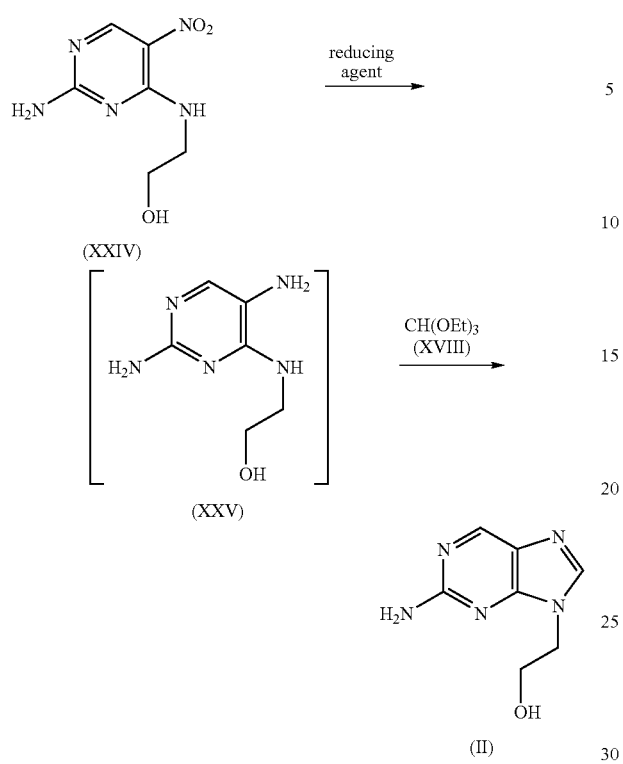

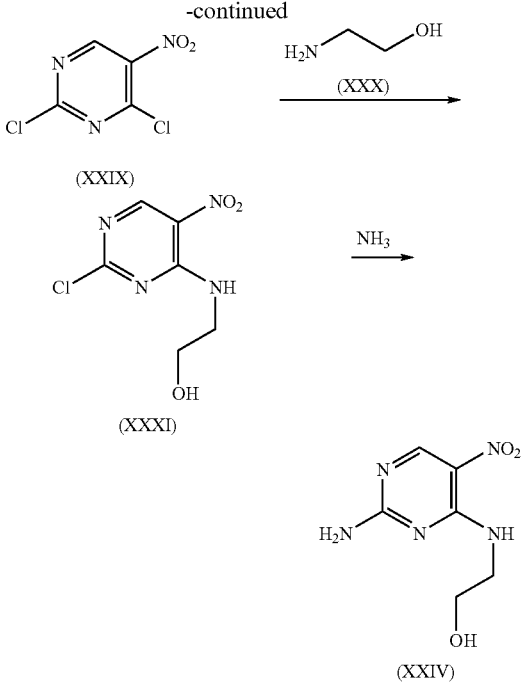

Preferred examples of the polar organic solvent, which is used in reaction scheme 7 above, are as described above.

Meanwhile, the compound of formula (XXIV) which is used in the preparation of the compound of formula (II) can be prepared in situ, and its preparation method, etc., are described in detail in Journal of organic chemistry 20, 171 (1955) and Journal of the Chemistry Society, 2821(1958).

The method of preparing the compound of formula (XXIV) will now be described in brief. As shown in reaction scheme (8), 5-nitrouracil of formula (XXVIII) is reacted with a chlorinating agent, such as phosphorus oxychloride, at a temperature of about 50-150° C., and preferably about 90-110° C., for about 1-10 hours, and preferably about 2-5 hours, to give 2,4-dichloro-5-nitropyrimidine of the following formula (XXIX). The compound of formula (XXIX) is then reacted with ethanolamine of formula (XXX) in a polar organic solvent at a temperature of about 0-100° C., and preferably about 10-20° C., for about 10-30 hours, and preferably about 15-20, to give 2-chloro-4-(2-hydroxyethylamino)-5-nitropyrimidine of formula (XXXI). Then, the compound of formula (XXXI) is reacted with ammonia in a polar organic solvent at a temperature of about 0-100° C., and preferably about 40-60° C., for about 10-20 hours, and preferably about 12-15 hours, to yield 2-amino-4-(2-hydroxyethylamino)-5-nitropyrimidine of formula (XXIV).

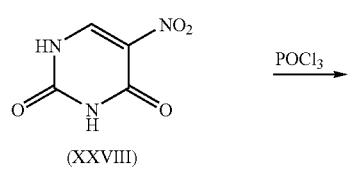

Preferred examples of the polar organic solvent which is used in reaction scheme (8) are as described above.

BEST MODE FOR CARRYING OUT THE INVENTION

The present invention will hereinafter be described in further detail by examples. It should however be borne in mind that the present invention is not limited to or by the examples.

Example 1

Preparation of 2,4-dichloro-5-nitropyrimidine 15.71 g (0.1 mole) of 5-nitrouracil was completely dissolved in 31.42 ml of phosphorus oxychloride, to which 22.39 g (0.15 mole) of diethylaniline was then added slowly at room temperature. The temperature within a reactor containing the mixture was elevated slowly to 105-110° C., and the mixture was stirred at this temperature for three hours. After completion of the reaction, the reaction product was concentrated under reduced pressure. The remaining concentrate was added to 150 ml of water slowly, and extracted three times with 200 ml portions of ethylether. The organic layer was collected, washed with 300 ml of water, dried with anhydrous magnesium sulfate, filtered and washed. The filtrate was concentrated under reduced pressure and distilled under reduced pressure, thereby giving 13.58 g (70% yield) of oily 2,4-dichloro-5-nitropyrimidine.

IR: $v_{max}$ (cm$^{-1}$): 3085, 1532, 1353, 1344, 1207, 1104

$H^1$ NMR (CDCl$_3$, 300 MHz)(ppm): 9.18 (1H, s, H of C-6)

Example 2

Preparation of 2,4-dichloro-5-nitropyrimidine 15.71 g (0.1 mole) of 5-nitrouracil was completely dissolved in 31.42 ml of phosphorus oxychloride, to which 18.78 g (0.15 mole) of dimethylaniline was then added slowly at room temperature. The temperature within a reactor containing the mixture was elevated slowly to 105-110° C., and the mixture was stirred at this temperature for five hours. After completion of the reaction, the reaction product was concentrated under reduced pressure. The remaining concentrate to added to 150 ml of water and then extracted three times with 200 ml portions of ethylether. The organic layer was collected, washed with 300 ml of water, dried with anhydrous magnesium sulfate, filtered and washed. The filtrate was concentrated under reduced pressure and distilled under reduced pressure, thereby giving 12.03 g (62% yield) of oily 2,4-dichloro-5-nitropyrimidine.

Spectrum data for the compound are the same as in Example 1.

Example 3

Preparation of 2-chloro-4-(2-hydroxyethylamino)-5-nitropyrimidine 19.40 g (0.1 mole) of 2,4-dichloro-5-nitropyrimidine was completely dissolved in 60 ml of methanol and maintained below 15° C. To this solution, a solution of 12.22 g (0.2 mole) of ethanolamine in 20 ml of methanol was added slowly while maintaining the temperature of a reactor below 20° C. The mixture was stirred below 15° C. for 18 hours. After completion of the reaction, the reaction product was maintained below 5° C., and the resulting crystal was filtered, washed and dried, thereby giving 18.58 g (85% yield) of light yellow-colored 2-chloro-4-(2-hydroxyethylamino)-5-nitropyrimidine.

Melting point: 123-125° C.
IR: $n_{max}$ (cm$^{-1}$): 3330, 3164, 1536, 1431, 1314, 1104
H$^1$ NMR (DMSO-D$_6$, 300 MHz)(ppm):
3.59-3.61 (2H, t, —NHCH$_2$CH$_2$—)
3.90-3.94 (2H, t, —NHCH$_2$CH$_2$—)
4.92 (1H, brs, —OH)
8.99-9.03 (2H, m, —NHCH$_2$CH$_2$— and H of C-6)

Example 4

Preparation of 2-chloro-4-(2-hydroxyethylamino)-5-nitropyrimidine 19.40 g (0.1 mole) of 2,4-dichloro-5-nitropyrimidine was completely dissolved in 60 ml of ethanol and maintained below 15° C. To this solution, a solution of 12.22 g (0.2 mole) of ethanolamine in 20 ml of methanol was added slowly while maintaining the temperature of a reactor below 20° C. The mixture was stirred below 15° C. for 18 hours. After completion of the reaction, the reaction product was maintained below 5° C., and the resulting crystal was filtered, washed and dried, thereby giving 17.71 g (81% yield) of light yellow-colored 2-chloro-4-(2-hydroxyethylamino)-5-nitropyrimidine.

Spectrum data for the compound are the same as in Example 3.

Example 5

Preparation of 2-amino-4-(2-hydroxyethylamino)-5-nitropyrimidine 21.86 g (0.1 mole) of 2-chloro-4-(2-hydroxyethylamino)-5-nitropyrimidine was dissolved in 500 ml of ethanol, and maintained between 50-60° C. A stream of ammonia was bubbled through the mixture for 13 hours. After completion of the reaction, the reaction product was maintained below 5° C., and the resulting crystal was filtered, washed and dried, thereby giving 18.92 g (95% yield) of light yells colored 2-amino-4-(2-hydroxyethylamino)-5-nitropyrimidine.

Melting point: 192-194° C.
IR: $n_{max}$ (cm$^{-1}$): 3341, 3337, 3314, 3104, 2981, 1531
H$^1$ NMR (DMSO-D$_6$, 300 MHz)(ppm):
3.30-3.34 (2H, t, —NHCH$_2$CH$_2$—)
3.54-3.59 (2H, t, —NHCH$_2$CH$_2$—)
4.90 (1H, brs, —OH)
7.63-7.70 (2H, d, —NH$_2$)
8.63 (1H, s, —NHCH$_2$CH$_2$—)
8.85 (1H, s, H of C-6)

Example 6

Preparation of 2-amino-4-(2-hydroxyethylamino)-5-nitropyrimidine 21.86 g (0.1 mole) of 2-chloro-4-(2-hydroxyethylamino)-5-nitropyrimidine was dissolved in 500 ml of ammonia saturated ethanol solution, and maintained between 50-60° C. A stream of ammonia was bubbled through the mixture for 13 hours. After completion of the reaction, the reaction product was maintained below 5° C., and the resulting crystal was filtered, washed and dried, thereby giving 18.81 g (93% yield) of light yellow-colored 2-amino-4-(2-hydroxyethylamino)-5-nitropyrimidine.

Spectrum data for the compound are the same as in Example 5.

Example 7

Preparation of 2-amino-9-(2-hydroxyethyl)purine 19.92 g (0.1 mole) of 2-amino-4-(2-hydroxyethylamino)-5-nitropyrimidine was suspended in 400 ml of methanol, to which 10 g of wet Raney nickel was then added. The mixture was stirred at a temperature of 30-40° C. for 3 hours. After completion of the reaction, the reaction product was filtered through nitrocellulose, followed by washing. The filtrate was concentrated under reduced pressure. To the remaining concentrate, 100 ml of triethylorthoformate and 10 ml of concentrated hydrochloric acid were added, and the mixture was stirred under reflux for 9 hours at a temperature of 80-90° C. After completion of the reaction, the product was cooled to room temperature, and 200 ml of ethylether was then added thereto. The resulting crystal was filtered, washed and dried, thereby giving 13.44 g (75% yield) of yellowish brown-colored 2-amino-9-(2-hydroxyethyl)purine.

Melting point: 173-175° C.
IR: $n_{max}$ (cm$^{-1}$): 3410, 3335, 3205, 2945, 1627, 1577
H$^1$ NMR (DMSO-D$_6$, 300 MHz)(ppm):
3.68-3.78 (2H, t, =NCH$_2$CH$_2$—)
4.00-4.16 (2H, t, =NCH$_2$CH$_2$—)
4.99 (1H, brs, —OH)
6.39-6.52 (2H, q, —NH$_2$)
7.99 (1H, s, H of C-8)
8.55 (1H, s, H of C-6)

Example 8

Preparation of 2-amino-9-(2-hydroxyethyl)purine 19.92 g (0.1 mole) of 2-amino-4-(2-hydroxyethylamino)-5-nitropyrimidine was suspended in 400 ml of acetic acid, to which 20 g of iron powder was then added. The mixture was stirred at a temperature of 30-40° C. for 3 hours. After completion of the reaction, the reaction product was filtered through nitrocellulose, followed by washing. The filtrate was concentrated under reduced pressure. To the resulting concentrate, 100 ml of triethylorthoformate and 10 ml of concentrated hydrochloric acid were added, and the mixture was stirred under reflux for 9 hours at a temperature of 80-90° C.

After completion of the reaction, the crude product was cooled to room temperature, and 200 ml of ethylether was added thereto. The resulting crystal was filtered, washed and dried, thereby giving 10.75 g (60% yield) of yellowish brown-colored 2-amino-9-(2-hydroxyethyl)purine.

Spectrum data for the compound are the same as in Example 7.

Example 9

Preparation of 2-amino-9-(2-bromoethyl)purine 17.92 g (0.1 mole) of 2-amino-9-(2-hydroxyethyl)purine was completely dissolved in 400 ml of acetonitrile, to which 84.42 g (0.20 mole) of dibromotriphenylphosphine was then added. The mixture was stirred for 5 hours at a temperature of 30-40° C. After completion of the reaction, 300 ml of water was added to the reaction product. The resulting solution was neutralized with aqueous sodium hydroxide solution and extracted four times with 500 ml portions of a mixed solution of chloroform and methanol (4:1). The organic layer was collected, and dried with anhydrous magnesium sulfate, followed by filtration and washing. The resulting filtrate was concentrated under reduced pressure, and crystallized from chloroform, 22.03 g (91%) of white 2-amino-9-(2-bromoethyl)purine.

Melting point: 192-194° C.
IR: $n_{max}$ (cm$^{-1}$): 3332, 3211, 2973, 1612, 1567, 1472
H$^1$ NMR (DMSO-D$_6$, 300 MHz)(ppm):
3.89-3.93 (2H, t, =NCH$_2$C$\underline{H}_2$—)
4.44~4.48 (2H, t, =NC$\underline{H}_2$CH$_2$—)
6.57 (2H, s, —NH$_2$)
8.09 (1H, s, H of C-8)
8.58 (1H, s, H of C-6)

Example 10

Preparation of 2-amino-9-(2-bromoethyl)purine 17.92 g (0.1 mole) of 2-amino-9-(2-hydroxyethyl)purine was completely dissolved in 200 ml of 1,4-dioxane. The solution was added with 49.75 g (0.15 mole) of carbon tetrabromide and cooled below 5° C. To the cooled material, 39.34 g (0.15 mole) of triphenylphosphine was added, followed by stirring for 5 hours at room temperature. After completion of the reaction, 300 ml of water was added to the reaction product, which was then extracted four times with 500 ml portions of a mixed solution of chloroform and methanol (4:1). The organic layer was collected, and dried with anhydrous magnesium sulfate, followed by filtration and washing. The resulting filtrate was concentrated under reduced pressure, and crystallized from chloroform, 15.74 g (65%) of white 2-amino-9-(2-bromoethyl)purine.

Spectrum data for the compound are the same as in Example 9.

Example 11

Preparation of 2-amino-9-(ethyl 2-carboethoxybutanoate-4-yl)purine 24.21 g (0.1 mole) of 2-amino-9-(2-bromoethyl)purine was completely dissolved in 120 ml of dimethylsulfoxide. To the solution, 48.05 g (0.3 mole) of diethylmalonate and 41.46 g (0.3 mole) of potassium carbonate were added, followed by stirring for four hours at a temperature of 40-50° C. After completion of the reaction, the product was cooled to room temperature, to which 300 ml of water then added. The resulting solution was extracted three times with 400 ml portions of dichloromethane. The organic layer was collected, and dried with anhydrous magnesium sulfate, followed by filtration and washing. The resulting filtrate was concentrated under reduced pressure and crystallized from butanol, thereby giving 27.31 g (85% yield) of light yellow-colored 2-amino-9-(ethyl 2-carboethoxybutanoate-4-yl)purine.

Melting point: 65-67° C.
IR: $n_{max}$ (cm$^{-1}$): 3337, 3204, 2953, 1743, 1730, 1631
H$^1$ NMR (DMSO-D$_6$, 300 MHz)(ppm):
1.09-1.14 (6H, t, —CH$_2$C$\underline{H}_3$ □ 2)
2.31-2.35 (2H, q, =NCH$_2$C$\underline{H}_2$CH=)
3.43~3.48 (1H, t, =NCH$_2$CH$_2$C$\underline{H}$=)
3.99-4.13 (6H, m, —C$\underline{H}_2$CH$_3$ □ 2 and =NC$\underline{H}_2$CH$_2$CH=)
6.50 (2H, s, —NH$_2$)
8.00 (1H, s, H of C-8)
8.55 (1H, s, H of C-6)

Example 12

Preparation of 2-amino-9-(ethyl 2-carboethoxybutanoate-4-yl)purine 24.21 g (0.1 mole) of 2-amino-9-(2-bromoethyl)purine was completely dissolved in 200 ml of dimethylformamide. To the solution, 48.05 g (0.3 mole) of diethylmalonate and 41.46 g (0.3 mole) of potassium carbonate were added, followed by stirring for four hours at a temperature of 40-50° C. After completion of the reaction, the product was cooled to room temperature, to which 300 ml of water was then added. The resulting solution was extracted three times with 400 ml portions of dichloromethane. The organic layer was collected, and dried with anhydrous magnesium sulfate, followed by filtration and washing. The resulting filtrate was concentrated under reduced pressure and crystallized from butanol, thereby giving 26.67 g (83% yield) of light yellow-colored 2-amino-9-(ethyl 2-carboethoxybutanoate-4-yl)purine.

Spectrum data for the compound are the same as in Example 11.

Example 13

Preparation of 2-amino-9-[4-hydroxy-3-(hydroxymethyl)but-1-yl]purine 32.13 g (0.1 mole) of 2-amino-9-(ethyl 2-carboethoxybutanoate-4-yl)purine was dissolved in 300 ml of t-butanol, and warmed to a temperature of 50-60° C., followed by the addition of 21.06 g (0.61 mole) of sodium borohydride. To the mixture, 30 ml of methanol was added slowly, followed by stirring for four hours. After completion of the reaction, the product was cooled to room temperature, neutralized with diluted hydrochloric acid, and then concentrated. The resulting concentrate was added to 100 ml of methanol and stirred for two hours at room temperature, followed by filtration. The filtrate was concentrated under reduced pressure and crystallized from butanol, thereby giving 18.98 g (80% yield) of offwhite-colored 2-amino-9-[4-hydroxy-3-(hydroxymethyl)but-1-yl]purine.

Melting point: 152-154° C.
IR: $n_{max}$ (cm$^{-1}$): 3432, 3336, 3215, 3007, 2964, 1638
H$^1$ NMR (DMSO-D$_6$, 300 MHz)(ppm):
1.41-1.49 (1H, m, =NCH$_2$CH$_2$C$\underline{H}$=)
1.75-1.86 (2H, q, =NCH$_2$C$\underline{H}_2$CH=)
3.33-3.42 (4H, m, —C$\underline{H}_2$OH □ 2)
4.07-4.13 (2H, t, =NC$\underline{H}_2$CH$_2$CH=)
4.40 (2H, brs, —CH$_2$O$\underline{H}$ □ 2)
6.51 (2H, s, —NH$_2$)
8.10 (1H, s, H of C-8)
8.60 (1H, s, H of C-6)

Example 14

Preparation of 2-amino-9-[4-hydroxy-3-(hydroxymethyl)but-1-yl]purine 32.13 g (0.1 mole) of 2-amino-9-(ethyl 2-carboethoxybutanoate-4-yl)purine was dissolved in 600 ml of dichloromethane, and warmed to a temperature of 50-60° C., followed by the addition of 21.06 g (0.61 mole) of sodium borohydride. To the mixture, 30 ml of methanol was added slowly, followed by stirring for four hours. After completion of the reaction, the product was cooled to room temperature, neutralized with diluted hydrochloric acid, and then concentrated. The resulting concentrate was added to 100 ml of methanol and then stirred for two hours at room temperature, followed by filtration. The filtrate was concentrated under reduced pressure and crystallized from butanol, thereby giving 18.96 g (80% yield) of offwhite-colored 2-amino-9-[4-hydroxy-3-(hydroxymethyl)but-1-yl]purine.

Spectrum data for the compound are the same as in Example 13.

Example 15

Preparation of 2-amino-9-[4-hydroxy-3-(hydroxymethyl)but-1-yl]purine 24.21 g (0.1 mole) of 2-amino-9-(2-bromoethyl)purine was completely dissolved in 120 ml of dimethylsulfoxide, to which 48.05 g (0.3 mole) of diethylmalonate and 41.46 g (03 mole) of potassium carbonate were then added. The mixture was stirred at a temperature of 40-50° C. for 4 hours. After completion of the reaction, the reaction product was cooled to room temperature, to which 300 ml of water was then added. The solution was then extracted three times with 400 ml portions of dichloromethane. The organic layer was collected, and dried with anhydrous magnesium sulfate, followed by filtration and washing. The filtrate was concentrated under reduced pressure. The remaining concentrate was added to 300 ml of t-butanol and then warmed to 60° C., followed by the addition of 21.06 g (0.61 mole) of sodium borohydride. To the resulting mixture, 30 ml of methanol was added slowly, followed by stirring for five hours. After completion of the reaction, the reaction product was cooled to room temperature, neutralized with diluted hydrochloric acid, and then concentrated. The remaining concentrate was added to 100 ml of methanol and then stirred for two hours at room temperature, followed by filtration. The filtrate was concentrated under reduced pressure and crystallized from butanol, thereby giving 13.05 g (55% yield) of light yellow-colored 2-amino-9-[4-hydroxy-3-(hydroxymethyl)but-1-yl]purine.

Spectrum data for the compound are the same as in Example 13.

Example 16

Preparation of 9-[4-acetoxy-3-(acetoxymethyl)but-1-yl]-2-aminopurine (famciclovir)

23.73 g (0.1 mole) of 2-amino-9-(4-hydroxy-3-(hydroxymethyl)but-1-yl)purine was suspended in 300 ml of tetrahydrofuran. To the suspension, 24.52 g (0.31 mole) of pyridine, 1.22 g (0.01 mole) of 4-dimethylaminopyridine and 21.44 g (0.21 mole) of acetic acid anhydride were added, and the mixture was stirred for five hours at room temperature. After completion of the reaction, the reaction product was concentrated under reduced pressure. The remaining concentrate was added to 300 ml of purified water and then extracted four times with 400 ml portions of chloroform. The organic layer was collected, and dried with anhydrous magnesium sulfate, followed by filtration and washing. The resulting filtrate was concentrated under reduced pressure and crystallized from butanol, thereby giving 24.10 g (75% yield) of white 9-[4-acetoxy-3-(acetoxymethyl)but-1-yl-2-aminopurine (famciclovir).

Melting point: 137-139° C.
IR: $n_{max}$ (cm$^{-1}$): 3330, 3160, 1743, 1728, 1645, 1606
$^1$H NMR (DMSO-d$_6$, 300 MHz)(ppm):
1.86-2.03 (9H, m, =NCH$_2$C$\underline{H}_2$CH= and —CH(CH$_2$OCOC$\underline{H}_3$)$_2$)
4.07 (4H, d, —CH(C$\underline{H}_2$OCOCH$_3$)$_2$)
4.16 (2H, t, =NC$\underline{H}_2$CH$_2$CH=)
6.38 (2H, brs, —NH$_2$)
8.06 (1H, s, H of C-8)
8.61 (1H, s, H of C-6)

Example 17

Preparation of 9-[4-acetoxy-3-(acetoxymethyl)but-1-yl]-2-aminopurine (famciclovir)

23.73 g (0.1 mole) of 2-amino-9-(4-hydroxy-3-(hydroxymethyl)but-1-yl)purine was suspended in 300 ml of tetrahydrofuran. To the suspension, 31.37 g (0.31 mole) of triethylamine, 1.22 g (0.01 mole) of 4-dimethylaminopyridine and 21.44 g (0.21 mole) of acetic acid anhydride were added, and the mixture was stirred for five hours at room temperature. After completion of the reaction, the reaction product was concentrated under reduced pressure. The remaining concentrate was added to 300 ml of purified water and then extracted four times with 400 ml portions of chloroform. The organic layer was collected, and dried with anhydrous magnesium sulfate, followed by filtration and washing. The resulting filtrate was concentrated under reduced pressure and crystallized from butanol, thereby giving 21.85 g (68% yield) of white 9-[4-acetoxy-3-(acetoxymethyl)but-1-yl-2-aminopurine (famciclovir).

Spectrum data for the compound are the same as in Example 16.

INDUSTRIAL APPLICABILITY

As described above, the preparation method according to the present invention allows famciclovir, a purine derivative drug with effective antiviral activity, to be prepared in a high selectivity of 100% in a pure form by using the inventive new compound of 2-amino-9-(2-substituted ethyl)purine. In addition, the inventive method allows the utilization of relatively mild reaction conditions, and thus, has high industrial process efficiency.

The invention claimed is:

1. A 2-amino-9-(2-bromoethyl)purine compound of the following formula (III-1):

(Formula III-1)

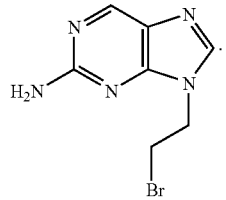

2. A method for the preparation of 9-[4-acetoxy-3-(acetoxymethyl)but-1-yl]-2-aminopurine, which comprises the steps of:
(a) reacting a compound of the following formula (II$^1$) with an halogenating agent in a polar or nonpolar organic solvent, to give 2-amino-9-(2-halogenoethyl)purine of the following formula (III); and (B) reacting the compound of formula (III) with a compound of the following formula (IV) in a polar organic solvent in the presence of a base, to give a compound of the following formula (V):

(Formula III)

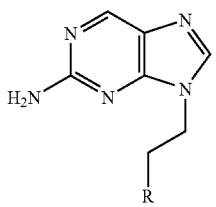

wherein R is a hydroxy, mexyloxy or tosyloxy group;

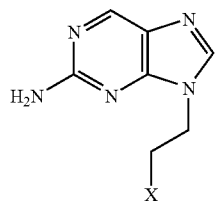

wherein X is a halogen atom;

(Formula IV)

(Formula V)

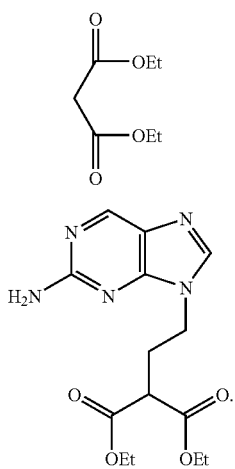

3. The method of claim 2, which further comprises, after the step (B), the steps of: (C) reacting the compound of formula (V) with a reducing agent in a polar or nonpolar organic solvent, to give a compound of the following formula (VI); and (D) reacting the compound of formula (VI) with acetic acid anhydride in a nonpolar organic solvent, to give a compound of the following formula (I):

(Formula I)

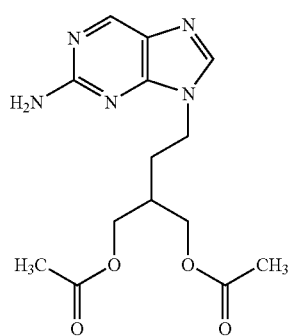

(Formula VI)

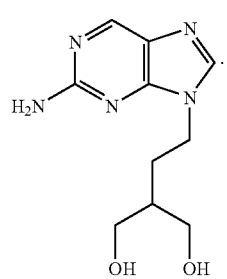

4. The method of claim 2, wherein the compound of formula (II') is a compound of the following formula (II), and the compound of formula (III) is a compound of the following formula (III-1):

(Formula II)

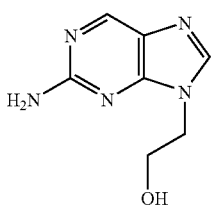

(Formula III-1)

5. The method of claim 2, wherein said halogenating agent comprises a member selected from the group consisting of carbon tetrachloride, sodium iodide, potassium iodide, dibromotriphenylphosphine, carbon tetrabromide and N-bromosuccinimide.

6. The method of claim 2, wherein said base comprises at least one member selected from the group consisting of potassium carbonate, sodium carbonate, sodium methoxide and sodium ethoxide.

7. The method of claim 2, wherein said polar solvent comprises at least one member selected from the group consisting of N,N-dimethylformamide, dimethylsulfoxide, acetonitrile, pyridine, acetic acid, and lower alcohol solvents with 1 to 3 carbon atoms.

8. The method of claim 2, wherein said nonpolar organic solvent comprises at least one member selected from the group consisting of ethylether, tetrahydrofuran, toluene, benzene, 1,4-dioxane, chloroform, and dichloromethane.

9. The method of claim 2, wherein the reaction is carried out at a temperature of 0-100° C.

10. The method of claim 3, wherein said halogenating agent comprises a member selected from the group consisting of carbon tetrachloride, sodium iodide, potassium iodide, dibromotriphenylphosphine, carbon tetrabromide and N-bromosuccinimide.

11. The method of claim 4, wherein said halogenating agent comprises a member selected from the group consisting of carbon tetrachloride, sodium iodide, potassium iodide, dibromotriphenylphosphine, carbon tetrabromide and N-bromosuccinimide.

12. The method of claim 3, wherein said base comprises at least one member selected from the group consisting of potassium carbonate, sodium carbonate, sodium methoxide and sodium ethoxide.

13. The method of claim 4, wherein said base comprises at least one member selected from the group consisting of potassium carbonate, sodium carbonate, sodium methoxide and sodium ethoxide.

14. The method of claim 3, wherein said reducing agent comprises a member selected from the group consisting of sodium borohydride and lithium aluminum hydride.

15. The method of claim 4, wherein said reducing agent comprises a member selected from the group consisting of sodium borohydride and lithium aluminum hydride.

16. The method of claim 3, wherein said polar solvent comprises at least one member selected from the group consisting of N,N-dimethylformamide, dimethylsulfoxide, acetonitrile, pyridine, acetic acid, and lower alcohol solvents with 1 to 3 carbon atoms.

17. The method of claim 4, wherein said polar solvent comprises at least one member selected from the group consisting of N,N-dimethylformamide, dimethylsulfoxide, acetonitrile, pyridine, acetic acid, and lower alcohol solvents with 1 to 3 carbon atoms.

18. The method of claim 3, wherein said nonpolar organic solvent comprises at least one member selected from the group consisting of ethylether, tetrahydrofuran, toluene, benzene, 1,4-dioxane, chloroform, and dichloromethane.

19. The method of claim 4, wherein said nonpolar organic solvent comprises at least one member selected from the group consisting of ethylether, tetrahydrofuran, toluene, benzene, 1,4-dioxane, chloroform, and dichloromethane.

20. The method of claim 3 wherein the reaction is carried out at a temperature of 0-100° C.

21. The method of claim 7, wherein said lower alcohol solvents with 1 to 3 carbon atoms comprises at least one member selected from the group consisting of methanol, ethanol, and isopropanol.

22. The method of claim 16, wherein said lower alcohol solvents with 1 to 3 carbon atoms comprises at least one member selected from the group consisting of methanol, ethanol, and isopropanol.

23. The method of claim 17 wherein said lower alcohol solvents with 1 to 3 carbon atoms comprises at least one member selected from the group consisting of methanol, ethanol, and isopropanol.

* * * * *